United States Patent [19]

Beranek

[11] Patent Number: 4,577,643
[45] Date of Patent: Mar. 25, 1986

[54] MOVABLE MULTI-CONTACT ELECTROMECHANICAL CONNECTION

[75] Inventor: William J. Beranek, Cooper City, Fla.

[73] Assignee: Cordis Corporation, Miami, Fla.

[21] Appl. No.: 608,785

[22] Filed: May 10, 1984

[51] Int. Cl.⁴ .............................................. A61N 1/04
[52] U.S. Cl. .................. 128/785; 128/419 P
[58] Field of Search ............... 339/5, 6, 8; 128/419 P, 128/784–786

[56] References Cited

U.S. PATENT DOCUMENTS

| | | | |
|---|---|---|---|
| 3,193,636 | 7/1965 | Daniels | 339/8 P |
| 3,205,468 | 9/1965 | Henschen . | |
| 3,396,586 | 8/1968 | Maclin et al. | 339/5 R |
| 3,568,660 | 3/1971 | Crites | 128/786 |
| 3,572,344 | 3/1971 | Bdduc | 128/786 |
| 3,731,671 | 5/1973 | Mageoh . | |
| 4,112,953 | 9/1978 | Shanker et al. | |
| 4,236,525 | 12/1980 | Sluetz et al. | 128/419 P |
| 4,258,725 | 3/1981 | O'Neill . | |
| 4,381,013 | 4/1983 | Dutcher | 128/786 |
| 4,411,277 | 10/1983 | Dickhudt | 128/784 |
| 4,463,765 | 8/1984 | Gold | 128/785 |
| 4,466,690 | 8/1984 | Osypka | 128/419 P |
| 4,484,586 | 11/1984 | McMickle et al. | 128/786 |

FOREIGN PATENT DOCUMENTS 2347720  9/1973  Fed. Rep. of Germany ...... 128/786

Primary Examiner—William E. Kamm
Assistant Examiner—Mitchell J. Shein
Attorney, Agent, or Firm—Lockwood, Alex, Fitzgibbon & Cummings

[57] ABSTRACT

An improved electrical connection capable of mechanical movement for providing an electrical connection between a rotatable terminal pin and an external pacer terminal casing in an improved cardiac pacer lead is disclosed. The pacer lead includes an elongated terminal pin at its proximal end that has a generally cylindrical cross-section which extends through an axial bore of an external retaining collar, a coupling and an insulating sleeve and terminates in engagement with an electrode at the distal end at the pacer lead. The retaining collar has a counterbore that defines an annular cavity between the collar and the terminal pin which accomodates an electrical connecting coil. The connection coil has a configuration wherein individual coil turns are circumferentially offset from adjacent coil turns and project radially outwardly from the axis of the coil. The coil is assembled over the terminal pin and within the collar counterbore so that the turns of the coil springly contact both the terminal pin and collar counterbore to create an electrical contact between them that allows rotation of the terminal pin within the collar.

20 Claims, 8 Drawing Figures

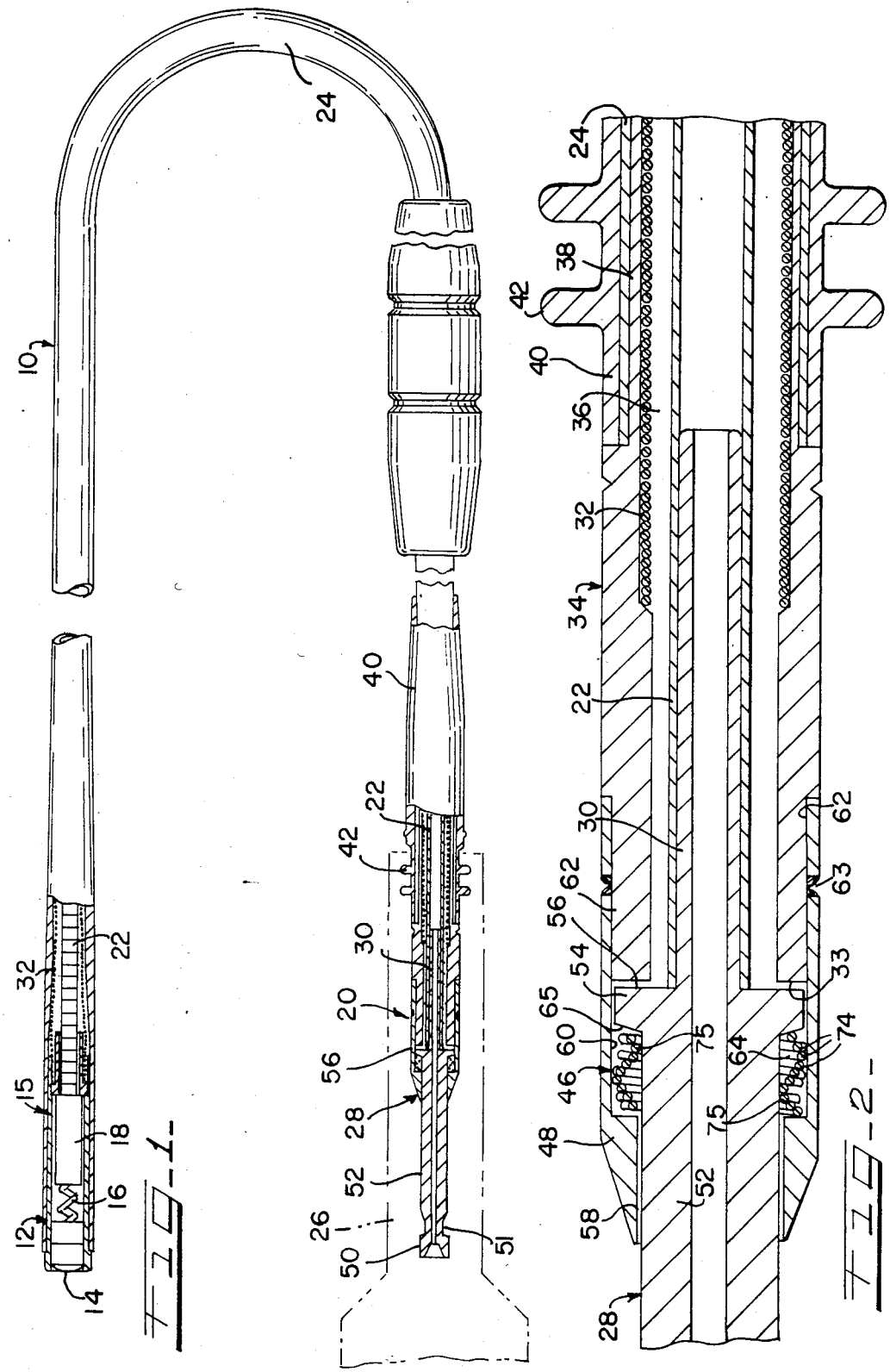

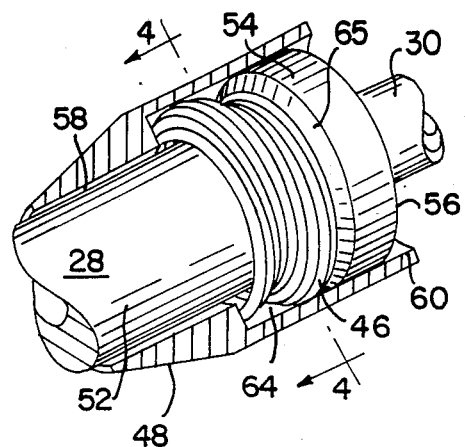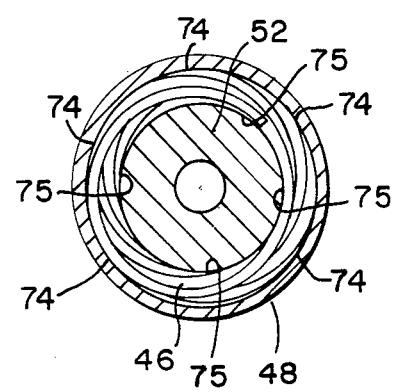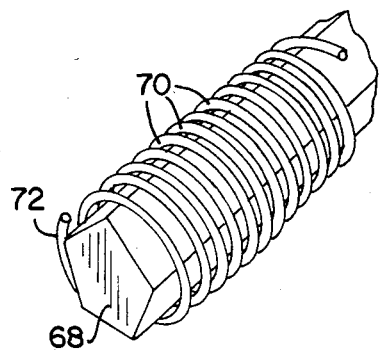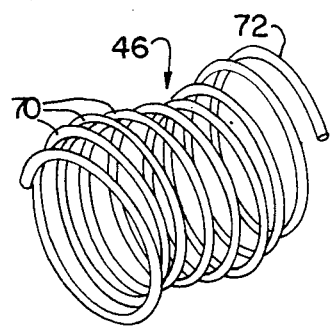

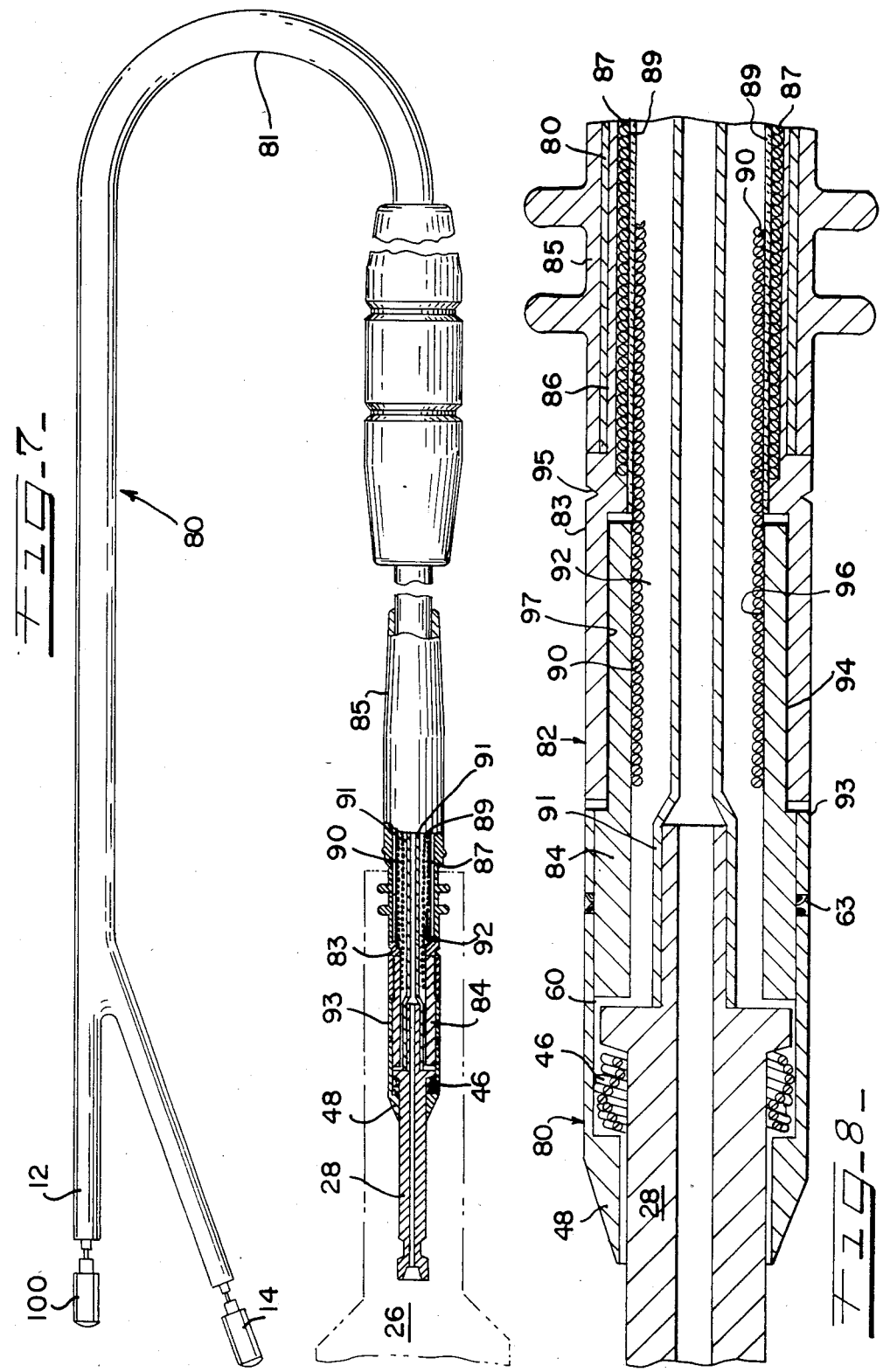

MOVABLE MULTI-CONTACT ELECTROMECHANICAL CONNECTION

BACKGROUND AND SUMMARY OF THE INVENTION

This invention generally relates to electrical connections capable of mechanical movement, and more particularly to an improved cardiac pacer lead incorporating an electromechanical connection for providing an electrical connection between a rotatable terminal pin and an external pacer terminal casing.

A conventional cardiac pacer lead includes an electrode at its distal end and a cardiac pacer or pulse generator terminal at its proximal end. The two ends are interconnected by an insulating sleeve or sheath that is inert to body fluids and that contains an electrical conductor therewithin. The distal end electrode, which may be porous, must be properly manipulated so that it is brought into contact with the cardiac tissue that it will subsequently activate. The surgeon implanting the pacer lead typically inserts the pacer lead into the patient by way of a surgical incision in the chest cavity and through appropriate body passageways for attachment of the electrode to cardiac tissue in an atrial or ventricular heart chamber. These insertion techniques are greatly facilitated by structuring the lead to permit rotation of the electrode within the insulating sleeve which is connected to the terminal end to allow the surgeon to properly position the electrode end by manipulating the terminal end which is exterior of the body so that the surgeon is certain that the electrode end of the pacer lead makes contact at the desired cardiac tissue location.

It therefore becomes desirable to equip cardiac pacer leads with a terminal end that, when rotated, will rotate the distal electrode. Due to this needed rotatability, it further becomes desirable to supply a pacer lead terminal pin with a reliable electrical connection that allows substantially unrestricted rotation of the terminal end and transmits current from the pacer through the terminal to the electrode.

One generally known method of obtaining such an electromechanical connection involves the use of "spring fingers" at the pacer lead proximal end, that is, a series of slender electrically conductive strips extending longitudinally from the pacer lead, each strip having a radially inwardly extending catch at its forwardmost end that engages an annular rib on the terminal pin shaft. This type of connection, although adequate and reliable, presents potential problems in that excessive pressure upon the spring fingers by the surgical team while handling or inserting the pacer lead can potentially deflect the spring fingers outwardly so that one or more of the spring fingers disengage the terminal end. Additionally, with this type of connection the terminal pin is not entirely contained within the pacer lead assembly. When this connection is flexed excessively, the spring fingers have a tendency to slightly separate from the terminal pin. It therefore becomes desirable to supply an improved electromechanical connection encased within a pacer lead terminal end that will allow unrestricted rotation of the pacer terminal pin within the terminal casing while providing a plurality of pressure contact points between the outer casing and the terminal pin.

The present invention provides this type of enhanced reliability in an electrical connection by providing a flexible and conductive coil that is deformed to provide a generally continuous but non-uniform helical shape in which individual turns of the coil adjacent one another randomly extend radially outwardly from the coil axis. In an important aspect of this invention, the coil is inserted over the terminal pin shaft of a pacer lead and retained on the terminal pin by an external casing that allows rotation of the terminal pin therein. Outward radial protrusions of the coil provide multiple contact points having proper contact pressure to electrically connect the terminal casing to the pacer terminal pin while allowing unrestricted rotation of the terminal pin within the casing. The coil has an inner diameter, as defined by the inwardlymost positioned turns, that is less than that of the terminal pin, and these inwardlymost positioned turns engage and continuously contact the pin.

It is accordingly a general object of the present invention to provide an improved multi-contact electromechanical connection.

Another object of this invention is to provide an improved electromechanical connection for use within a cardiac pacer lead wherein the proximal end terminal pin is capable of unrestricted rotating movement.

A further object of this invention is to provide an improved pacer lead having an electromechanical connection entirely contained within the pacer proximal end casing that allows rotation of the cardiac terminal pin.

Another object of the present invention is to provide a compact electromechanical connecting assembly that is especially suitable for a pacing lead having bipolar electrodes.

A still further object of this invention is to provide a multi-contact electomechanical connection incorporating a springwire coil having a non-uniformly deformed generally helical shape such that individual coil turns adjacent one another are generally radially spaced from one another to create a plurality of internal and external electrical contact points.

Another object of the present invention is to provide a compact electromechanical connection that has a minimal longitudinal extent.

These and other objects of the present invention will become apparent from the following detailed description of this invention, taken in conjunction with accompanying drawings, wherein:

FIG. 1 is an elevational view, partly cutaway, of a cardiac pacer lead incorporating a preferred embodiment of the invention;

FIG. 2 is an enlarged sectional view of the proximal end of the device illustrated in FIG. 1;

FIG. 3 is a cutaway perspective view of the terminal end of the pacer lead illustrated in FIG. 1 showing the position of the electromechanical connection assembly;

FIG. 4 is a section along line 4—4 of FIG. 3;

FIG. 5 is a perspective view illustrating the coil of the electromechanical connection assembly being formed upon a non-circular mandrel;

FIG. 6 is a perspective view of the coil illustrated in FIGS. 4 and 5 after it has been removed from the mandrel and before it has been incorporated into the electromechanical connector assembly.

FIG. 7 is an elevational view, partly cutaway, of a bipolar cardiac pacer lead incorporating an electromechanical connection assembly of the invention; and FIG. 8 is an enlarged sectional view of the proximal end of the device illustrated in FIG. 7.

DETAILED DESCRIPTION OF THE INVENTION

An improved cardiac pacer lead constructed in accordance with the principles of the present invention is illustrated in FIGS. 1-2. In particular, FIG. 1 describes a cardiac pacer lead 10 of generally conventional construction having a proximal end 20 and a distal end 12. Distal end 12 terminates in an electrode assembly 15 containing an electrode 14 and a wire screw 16 that facilitates maneuvering of the electrode 14 into contact with cardiac tissue.

Wire screw 16 is initially contained within an end guide 18 of the electrode assembly 15 and is extended during implantation upon rotation of wire screw 16. Such rotation is effected when the surgeon maneuvers the proximal end 20 of the device. The end guide 18 is attached to a flexible metal ribbon wound in a coil 22 that is enclosed in a flexible insulating sleeve 24 and that extends the length of the insulating sleeve 24 to a pin terminal 28 at the proximal end 20. Pin terminal 28 inserts into a cardiac pacer or pulse generator 26, shown in phantom. Ribbon coil 22 is connected to pin terminal 28, such as by insertion of a shaft end 30 of the pin terminal 28 into the proximal end of the ribbon coil 22, the ribbon coil 22 tightly engaging the pin terminal shaft end 30.

The electrode 14 at the distal end 12 of the pacer lead 10 transmits an electrical current impulse to stimulate the cardiac tissue. The surgeon implants the pacer lead 10 by inserting it through a surgical incision and body passageways until the electrode assembly 15 enters the intended heart chamber. Terminal pin 28 is rotatable at the proximal end 20 and correspondingly rotates the ribbon coil 22 and, when provided, the wire screw 16, in order to enhance the ability of the surgeon to maneuver the electrode 14 into contact with the heart tissue in the chamber.

An electrical connection is maintained between the electrode 14 and the proximal end 20 by means of a quadrafilar coil 32 formed of an electrically conductive material connected to the electrode assembly 15 at the distal end 12 of the pacer lead 10. The quadrafilar coil 32 is generally cylindrical in shape, extends longitudinally within the insulating sleeve 24 and is connected to the proximal end 20 at a terminal coupling 34. The terminal coupling 34 is electrically connected to the terminal pin 28. Quadrafilar coil 32 is disposed concentrically and outwardly of ribbon coil 22 within the insulating sleeve 24. An annular gap 36 is defined between the conductive coil 32 and the rotatable ribbon coil 22. Gap 36 ensures that ribbon coil 22 will rotate substantially unrestrictedly within the insulating sleeve 24 when the terminal pin 28 is turned.

The insulating sleeve 24 is typically fabricated from a flexible material inert to body fluids such as silicone, polyurethane or other non-reactive material. Sleeve 24 generally encases the electrode assembly 15 at the distal end 12 and is adhered to the proximal-end terminal coupling 34, such as to an axial lip 38 thereof. A flexible boot 40 having resilient annular ribs 42 and typically molded of Silastic rubber or the like, covers both the proximal end of the insulating sleeve 24 and the axial lip 38 of the terminal coupling 34. Boot 40 inserts into a female receptacle, not shown, of pulse generator 26 and prevents the body fluids from entering into the pulse generator 26.

When the pacer lead 10 is inserted into the female receptacle of pulse generator 26, electrical contact is established, in accordance with generally known assembly techniques, between the pulse generator 26 and the terminal pin 28. A multi-contact electromechanical assembly is provided for transmitting electrical current between the terminal pin 28 and the quadrafilar coil 32 within insulating sleeve 24, which is in current passing communication with the distal end electrode 14, while allowing the terminal pin 28 to freely rotate so that the electrode 14 can be rotated or otherwise positioned by maneuvering the proximal end 20 of pacer lead 10.

Referring more particularly to the multi-contact electromechanical assembly, such includes a connecting coil generally designated as 46 that is constructed in accordance with the principles of the present invention. The coil 46 is mounted over the terminal pin 28 and is retained within an external collar 48 which overlies the coil 46. Proximal end 44 of the terminal pin 28 projects out of an opening 49 of the collar 48. Collar 48 is connected to the terminal coupling 34, to provide a path for electrical current to flow from the pulse generator 26 to the to terminal pin 28, through the connecting coil 46, the collar 48 and to the coupling 34, which is in electrical communication with the quadrafilar coil 32 and the electrode 14 embedded in the heart tissue to provide cardiac stimulation of the patient.

Terminal pin 28 has a generally cylindrical shape and includes a main shaft 52 having a terminal contact nib 50. A rib 51 of the terminal pin 28 engages a detent in the pacer female receptacle, not shown, to maintain electrical contact between the terminal pin 28 and the pacer or pulse generator 26. The shaft end 30 axially extends from the distal end of the terminal pin 28. An outwardly radially extending skirt portion 54 which separates the main shaft 52 from the shaft distal end 30, has an outer diameter that is greater than that of the main shaft 52. A distal face 56 of the skirt portion 54 and a proximal end 56 of the terminal coupling 34 are preferably polished or burnished to remove any major surface irregularities so that the terminal pin 28 can freely rotate without interference or excessive frictional contact with the terminal coupling 34.

Retaining collar 48 which is generally cylindrically shaped, has an axial bore 58 having a diameter slightly greater than the outer diameter of terminal pin main shaft 52 so as to allow free rotation of the terminal pin 28 therein. An axial counterbore 60 adjacent to the axial bore 58 has an inner diameter slightly greater than the outer diameter of the terminal pin skirt portion 54 so that the skirt portion 54 is free to rotate with respect to the counterbore 60, this inner diameter of the counterbore 60 being substantially the same as the outer diameter of the proximal portion of the terminal coupling 34, which may include the illustrated indent 62. The counterbore 60 is dimensioned within retaining collar 48 so as to define an annular cavity 64 within which the connecting coil 46 is positioned to provide the electromechanical connection between the terminal pin 28 and the retaining collar 48. Connecting coil 46 is seated upon the main shaft 52 of terminal pin 28 adjacent to an inclined proximal face 65 of the skirt portion 54.

Connecting coil 46 needs to satisfy a minimum of two criteria. Firstly, it must allow free and relatively unrestricted rotational movement of the terminal pin 28 within the retaining collar 48. Also, the connecting coil 46 must provide a reliable electrical contact between the terminal pin 28 and the retaining collar 48 so as to consistently transmit electrical current from the pulse generator 26 to the distal end electrode 14. Additionally, due to the small size of typical pacer leads, the connecting coil 46 must itself be small and have a minimal axial length and radial extent.

The distal end of retaining collar counterbore 60 mates with indent 62 of the terminal coupling 34 and is joined to the coupling 34 by a weld 63, or other method of joining, such as a crimp, snap ring or O-ring. When so joined, the connecting coil 46 is entirely contained within the annular cavity 64, being unexposed and covered by the retaining collar 48. Terminal pin 28, retaining collar 48 and terminal coupling 34 are preferably fabricated from the same electrically conductive and non-corroding material, such as stainless steel or a stainless steel alloy.

FIGS. 7 and 8 illustrate the use of the preferred embodiment of the invention in a bipolar cardiac pacer lead, that is, one having two electrodes at its distal end for electrical stimulation of two areas of cardiac tissue by two separate electrical impulses.

FIG. 8 illustrates the proximal end of a bipolar cardiac pacer lead. The pacer lead 80 is similiar in overall construction to the unipolar pacer lead illustrated in FIGS. 1 and 2 and described above but differs from such a lead in that two paths for current flow electrically isolated from one another are provided down the length of the insulating sheath 81.

Such a construction provides a two-piece coupling assembly 82 containing a distal sleeve 83 and a proximal sleeve 84 that overlie one another while being insulated from each other. The insulating sheath 81 and boot 85 are fabricated from insulating materials such as those described and are seated upon an axially extending indent 86 of the distal sleeve 83. A first quadrafilar coil 87 of an electrically conductive material extends longitudinally within the insulating sheath 81 along its inner diameter 88. A second, inner insulating sheath 89 lies longitudinally and coaxially within the first conducting coil 87 to electrically insulate it from a second and inner quadrafilar coil 90.

The second coil 90 also transmits current from the pulse generator 26 to a second electrode 100 that contacts an area of cardiac tissue apart from that area contacted by the first electrode 14. The coil 90 is generally cylindrical in shape and extends longitudinally within the second insulating sheath 89 and also is connected to the distal sleeve 83 of the coupling assembly 82 by contacting a lip 96 at the distal end of the sleeve 83. Both quadrafilar coils 87 and 90 are disposed concentrically and outwardly of ribbon coil 91 within the insulating sheath 81. An annular gap 92 is defined between the inner, second conductive coil 90 and the rotatable ribbon coil 91. This gap 92 extends throughout both the length of the insulating sheath 81 and the coupling assembly 82.

The coupling assembly distal sleeve 83 and proximal sleeve 84 are insulated from each other by a very thin layer 93 of electrically non-conductive insulating material such as parylene. This thin layer 93 can be applied by either dipping one of the coupling sleeves 83 or 84 in the insulating material or by premolding an insulating endcap, not shown, that is sized to receive either the proximal sleeve indent 94 or the inner bore 97 of distal sleeve 83 and subsequently inserting it therein. The thickness of the insulating layer 93 in chosen such that when the proximal sleeve 84 is pressed into the distal sleeve 83, a substantially rigid connection is maintained between the two.

The retaining collar 48, terminal pin 28 and connecting coil 46 are all constructed the same as described hereinabove. The distal end of the retaining collar counterbore 60 mates with the coupling proximal sleeve 84 and is joined to the retaining collar 60 by a weld 63 or other method of joining, such as a crimp, snap ring or O-ring.

When inserted into a pulse generator that is adapted to deliver two separate electrical impulses, the terminal pin 28 engages an electrical contact collar and is held in place with a set screw, not shown. Current is transmitted from the pulse generator 26 to the terminal pin 28 through the connecting coil 46, the collar 48, and to the coupling assembly proximal sleeve 84 which is in electrical communication with the inner quadrafilar coil 90 that electrically communicates with one of the two distal end electrodes 14 and 100 embedded in the heart tissue of the patient.

While inserted in the pulse generator 26 the distal sleeve 83 engages a ring electrode, not shown, within the receptacle of the pacer. The ring electrode contacts the distal sleeve 83 just forward of 'V-notch' 95. Current is transmitted from the pacer ring electrode of the pulse generator to the coupling assembly distal sleeve 83 which is in electrical communication with the outer quadrafilar coil 87 that electrically communicates with the other distal end electrode 100 embedded in an area of heart tissue that is not contacted by the first electrode 14.

The contained connecting coil 46 utilized in both the unipolar and bipolar leads shown in the drawings is formed by winding electrically conductive springwire 72 tightly around the perimeter of a mandrel 68 having a non-circular cross-section, such as the pentagonal cross-section illustrated in FIG. 5. Other non-circular cross-sectional shapes are also suitable, such as rectangles and ellipses. Mandrel 68, which can be rotated during this process, has a cross sectional perimeter that is less than that of the terminal pin main shaft 52. The springwire 72 is tightly wound around the mandrel 68 under tension so that during the winding process a slight amount of tension is thereby imparted to the springwire 72, and it temporarily takes on a shape that approximates, but typically does not precisely coincide with, the cross-sectional perimeter of the mandrel 68.

When the mandrel 68 is subsequently removed, residual tension within the wound springwire 72 results in springback of individual turns 70 of the springwire 72 to form the coil 46 having a shape as illustrated in FIG. 6. Due to this springback, the deformed springwire individual turns 70 unwind slightly and rotate with respect to adjacent turns. The non-circular cross-section of the mandrel 68 imparts a deformation to each individual turn 70.

This springback results in a coil 46 that is deformed throughout the length of the springwire 72, and in which individual turns 70 are circumferentially offset from adjacent turns 70 and are radially spaced from the coil axis, as best seen in FIGS. 3, 4 and 6. The deformed coil 46 is non-symmetrical about its axis and has a configuration generally approximating that of a helix. The combination of the radial projection and rotational displacement of the individual turns 70 provides a plurality of external contact points 74 and a plurality of internal contact points 75.

As best seen in FIGS. 2 and 3, when the coil 46 is structured for inclusion within the proximal terminal assembly of the pacer lead 10, the external contact points 74 project from the central axis of the uninstalled coil 46 for a radial distance that is greater than the radius of the counterbore 60. When the coil 46 is installed, the external contact points 74 engage the counterbore 60 and compress the coil 46 at these external contact points 74. In this embodiment, the internal contact points 75 project from the central axis of the uninstalled coil 46 for a radial distance that is less then the radius of the main shaft 52 of the terminal pin 28. When the coil 46 is installed over the main shaft 52, the internal contact points 75 are urged outwardly. Each individual turn 70 of the connecting coil will undergo compressive stress so that connecting coil 46 is under a uniform stress along its entire length, ensuring a high contact pressure upon the terminal pin main shaft 52 and the collar 48, thus establishing a reliable and consistent electrical contact irrespective of the extent of rotational movement of the terminal pin 28.

Connecting coils of the type hereinabove described can be easily manufactured in extremely small sizes to accommodate correspondingly sized pins for use in various devices wherein an electrical contact must be maintained between a rotatable pin and its external casing. Numerous other embodiments of this invention will be apparent to those skilled in the art, especially with respect to the pacer leads within which electromechanical connection is included, without departing from the spirit and scope of this invention. Therefore, this invention is to be defined only by the appended claims.

What I claim is:

1. An improved cardiac pacer lead of the type having an electrode at its distal end for attachment to and the transmittal of an electrical impulse to cardiac tissue, a terminal at its proximal end for insertion into a cardiac pulse generator adapted to generate an electrical impulse, and an insulating sleeve interconnecting the distal end to the proximal end containing means to transmit electrical current from said pulse generator to said electrode and means to rotate said electrode from said terminal end, the improvement comprising:

an elongated terminal pin at the proximal end of said lead having a generally cylindrical cross-section, said terminal pin extending into said insulating sleeve and engaging said electrode rotating means;

an elongated coupling having a generally cylindrical cross-section and defining an annular passage therewithin, said coupling engaging said current transmitting means at one end;

external retaining means including a collar member having an axial bore therewithin and further having a counterbore, both said bore and counterbore adapted to receive said terminal pin, said counterbore defining an annular cavity between said collar member and said terminal pin within said collar member, said terminal pin extending through said bore and counterbore and contained within said collar member, said terminal pin being capable of rotation within said collar member, said collar member engaging said coupling; and a multi-contact electromechanical connection having a connector coil disposed within said collar member annular cavity, said connector coil being a mandrel-wound and tension-deformed length of springwire having a configuration wherein a plurality of individual coil turns are circumferentially offset from adjacent wound coil turns and project radially outwardly from the axis of said coil and springingly contact said collar member counterbore to create an electrical contact between said collar member and said terminal pin while allowing rotation of said terminal pin within said collar.

2. The improved cardiac pacer lead of claim 1, wherein said terminal pin includes a radially outwardly extending skirt portion intermediate said terminal pin.

3. The improved cardiac pacer lead of claim 1, wherein said coupling coaxially receives said terminal pin in said coupling annular passageway.

4. The improved cardiac pacer lead of claim 1, wherein said connector coil is disposed generally coaxially with respective said collar member and said terminal pin.

5. The improved cardiac pacer lead of claim 1, wherein said connector coil is composed of an electrically conductive springwire.

6. The improved cardiac pacer lead of claim 1, wherein said collar member, coupling, terminal pin and connector coil are composed of either a stainless steel or an alloy thereof.

7. The improved cardiac pacer lead of claim 1, wherein said collar member is secured to said coupling assembly, to contain said terminal pin within said collar and said coupling.

8. An electromechanical connector for forming an electrical and mechanical connection within a device having an element adapted for rotational movement with respect to a conductor, wherein the connector comprises:

a rotatable element;

a housing element overlying at least a portion of said rotatable element, an annular cavity defined by said rotatable element and said housing element; and a connector coil located within said annular cavity, said connector coil having a continuous deformed shape to provide said coil with a plurality of contact points between said rotatable element and said housing element, whereby electrical current is transmitted between said rotatable element and said housing element and whereby said rotatable element is capable of rotating within said housing element and the conductor, and said connector coil is a wound length of resilient springwire that had been tightly wound under tension around a generally non-circular mandrel and released into said continuous deformed shape that approximates the shape of a helical coil and that has individual adjacent coil turns which are rotated with respect to each other.

9. The electromechanical connector of claim 8, wherein the inner diameter of said connector coil is less than the outer diameter of said rotatable element and the general outer diameter of said connector coil is greater than the general inner diameter of said housing element.

10. A method for producing an improved cardiac pacer lead having a pulse generator terminal at its proximal end and a pulse-transmitting electrode at its distal end with a rotatable multi-contact eletromechanical connection joining the pulse generator terminal end to means for transmitting electrical current, said current transmitting means further connected to said pulse transmitting electrode, comprising:

providing a pulse generator terminal pin assembly including a terminal pin having an elongate shaft;

inserting the terminal pin assembly into a proximal opening of a flexible insulated conductor;

forming a multi-contact electromechanical connection coil by winding, under tension, a coil of electrically conductive springwire onto means for deforming the shape of the springwire coil, the deforming means having a cross-sectional configuration smaller than that of the terminal pin shaft, and removing said springwire coil from said deforming means, whereby individual turns of said springwire coil expand radially outwardly and the entire coil thereby assumes a deformed shape;

inserting the deformed connection coil coaxially onto said terminal pin shaft;

retaining said spring wire connector coil on said terminal pin shaft and rotatably retaining said terminal pin assembly in said pacer lead insulating sleeve by inserting an exterior retaining casing over said terminal pin, said retaining step including forming an inner annular cavity having an outer diameter less than the general outer diameter of said spring wire connector coil whereby the deformed radial shape of said coil springingly contacts both said retaining casing and said terminal pin at a plurality of points; and connecting said retaining casing to said flexible insulated conductor whereby current can be transmitted from said pulse generator through said terminal pin and through said flexible insulated conductor to said pulse transmitting electrode.

11. The method of claim 10, wherein said coil deformed shape generally approximates that of a helical coil.

12. The method of claim 10, wherein said deforming means is a mandrel having a substantially non-circular cross-section.

13. The method of claim 10, wherein said connecting step includes providing a terminal coupling in electrical engagement with said retaining casing and said flexible insulated conductor.

14. An improved bipolar cardiac pacer lead of the type having two electrodes at its distal end for attachment to and the transmittal of two separate electrical impulses to two distinct areas of cardiac tissue, a terminal at its proximal end for insertion into a cardiac pulse generator adapted to generate two electrical impulses, and an insulating sleeve interconnecting the distal end of the lead to the proximal end of the lead, the insulating sleeve containing means to transmit two separate electrical currents from said pulse generator to said respective electrodes and means to rotate said electrode from said terminal end, the improvement comprising:

an elongated terminal pin at the proximal end of said lead having a generally cylindrical cross-section, said terminal pin extending into said insulating sleeve and engaging said electrode rotating means;

an elongated coupling assembly having a generally cylindrical cross-section and defining an annular passage therewithin, said coupling assembly having two electrically conductive coupling members that are electrically insulated from each other, each of said coupling members engaging separate current transmitting means;

external retaining means including a collar member having an axial bore therewithin and further having a counterbore, both said bore and counterbore adapted to receive said terminal pin, said counterbore defining an annular cavity between said collar member and said terminal pin within said collar member, said terminal pin extending through said bore and counterbore and contained within said collar member, said terminal pin being capable of rotation within said collar member, said collar member engaging one of said coupling members; and a multi-contact electromechanical connection having a connector coil disposed within said collar member annular cavity, said connector coil having a configuration wherein a plurality of individual coil turns are circumferentially offset from adjacent turns and project radially outwardly from the axis of said coil and springingly contact said collar member counterbore to create an electrical contact between said collar member and said terminal pin while allowing rotation of said terminal pin within said collar.

15. The improved bipolar cardiac pacer lead of claim 14, wherein said coupling assembly includes two sleeve portions each sleeve portion having a generally cylindrical cross-section defining an annular passage therewith, said sleeve portions engaging each other to provide a substantially rigid connection therebetween, and said coupling assembly sleeve portions being electrically insulated from each other.

16. The improved bipolar cardiac pacer lead of claim 14, wherein said terminal pin includes a radially outwardly extending skirt portion intermediate said terminal pin.

17. The improved bipolar cardiac pacer lead of claim 14, wherein said coupling assembly coaxially receives said terminal pin in said coupling annular passageway.

18. The improved bipolar cardiac pacer lead of claim 14, wherein said connector coil is composed of an electrically conductive springwire.

19. The improved bipolar cardiac pacer lead of claim 14, wherein said connector coil is a wound length of springwire that had been wound under tension around a generally non-circular mandrel having an outer diameter less than that of said terminal pin, and said wire coil has a continuous deformed shape that is approximately that of a helical coil and that has individual adjacent coil turns which are rotated with respect to each other.

20. The improved bipolar cardiac pacer lead of claim 19, wherein said mandrel is substantially rectangular in cross-sectional shape.

* * * * *